US012578337B2

(12) United States Patent
Nakamura

(10) Patent No.: US 12,578,337 B2
(45) Date of Patent: Mar. 17, 2026

(54) METHOD FOR PROGNOSIS PREDICTION OF SKIN CANCER AND USE THEREOF

(71) Applicant: PUBLIC UNIVERSITY CORPORATION NAGOYA CITY UNIVERSITY, Nagoya (JP)

(72) Inventor: Motoki Nakamura, Nagoya (JP)

(73) Assignee: PUBLIC UNIVERSITY CORPORATION NAGOYA CITY UNIVERSITY, Nagoya (JP)

( * ) Notice: Subject to any disclaimer, the term of this patent is extended or adjusted under 35 U.S.C. 154(b) by 734 days.

(21) Appl. No.: 17/918,704

(22) PCT Filed: Apr. 1, 2021

(86) PCT No.: PCT/JP2021/014174
§ 371 (c)(1),
(2) Date: Oct. 13, 2022

(87) PCT Pub. No.: WO2021/210416
PCT Pub. Date: Oct. 21, 2021

(65) Prior Publication Data
US 2023/0147040 A1     May 11, 2023

(30) Foreign Application Priority Data

Apr. 15, 2020    (JP) ................................. 2020-072636

(51) Int. Cl.
| | |
|---|---|
| *G01N 33/5751* | (2026.01) |
| *C12Q 1/26* | (2006.01) |
| *C12Q 1/6886* | (2018.01) |
| *G01N 33/50* | (2006.01) |

(52) U.S. Cl.
CPC ........... *G01N 33/5751* (2026.01); *C12Q 1/26* (2013.01); *C12Q 1/6886* (2013.01); *C12Y 101/01049* (2013.01); *G01N 33/5011* (2013.01); *C12Q 2600/118* (2013.01); *C12Q 2600/158* (2013.01); *G01N 2333/904* (2013.01)

(58) Field of Classification Search
None
See application file for complete search history.

(56) References Cited

FOREIGN PATENT DOCUMENTS

| | | |
|---|---|---|
| CN | 110358821 A | 10/2019 |
| EP | 0 154 276 A2 | 9/1985 |
| EP | 0 154 276 A3 | 9/1985 |
| JP | 2007-519903 A | 7/2007 |
| JP | 5984324 B2 | 9/2016 |

OTHER PUBLICATIONS

Paul, E. Arch Derm Res. 1975. 254:159-174. (Year: 1975).*
Chen et al., "Metabolic classification of circulating tumor cells as a biomarker for metastasis and prognosis in breast cancer", Journal of Translational Medicine, 2020, vol. 18, No. 59, p. 1-14.
International Search Report, issued in PCT/JP2021/014174, PCT/ISA/210, dated Jun. 22, 2021.
Jiang et al., "Increased glycolysis correlates with elevated immune activity in tumor immune microenvironment", EBioMedicine, 2019, vol. 42, total 12 pages.
Li et al., "A New G6PD Knockdown Tumor-Cell Line with Reduced Proliferation and Increased Susceptibility to Oxidative Stress", Cancer Biotherapy & Radiopharmaceuticals, 2009, vol. 24, No. 1, p. 81-90.
Lipson et al., "PD-L1 Expression in the Merkel Cell Carcinoma Microenvironment: Association with Inflammation, Merkel Cell Polyomavirus, and Overall Survival", Cancer Immunol Res; 1 (1) Jul. 2013, p. 54-63.
Madore et al., "PD-L1 expression in melanoma shows marked heterogeneity within and between patients: implications for anti-PD-1/PD-L1 clinical trials", Pigment Cell & Melanoma Research, May 2015, vol. 28, No. 3, total 10 pages.
Nagashio et al., "Prognostic significance of G6PD expression and localization in lung adenocarcinoma", Biochim Biophys Acta Proteins Proteom. 2019, total 39 pages.
Nakamura et al., "Heterogeneity of PD-L1 Expression in a Case of Merkel Cell Carcinoma Exhibiting Complete Regression After Multiple Metastases", Br J Dermatol., 2019, total 5 pages.
Nakamura et al., "Increased programmed death ligand-1 expression in metastatic Merkel cell carcinoma associates with better prognosis", Journal of Dermatological Science 97 (2020), p. 165-167.
Wang et al., "Glucose-6-phosphate dehydrogenase expression is correlated with poor clinical prognosis in esophageal squamous cell carcinoma". Eur J Surg Oncol (2015), vol. 41, No. 10, total 7 pages.
Written Opinion of the International Searching Authority, issued in PCT/JP2021/014174, PCT/ISA/237, dated Jun. 22, 2021.
Xiao et al., "Glutathione Metabolism in Renal Cell Carcinoma Progression and Implications for Therapies", International Journal of Molecular Sciences, 2019, 20: 3672, total 20 pages.
Hu et al., "Variant G6PD levels promote tumor cell proliferation or apoptosis via the STAT3/5 pathway in the human melanoma xenograft mouse model," BMC Cancer, vol. 13, No. 251, 2013, pp. 1-11.
Nakamura et al., "Glucose-6-phosphate dehydrogenase correlates with tumor immune activity and programmed death ligand-1 expression in Merkel cell carcinoma," Journal for ImmunoTherapy of Cancer, vol. 8, e001679, 2020, pp. 1-10.
Supplementary European Search Report for European Application No. 2178754.4, dated Apr. 12, 2024.

* cited by examiner

*Primary Examiner* — Ruixiang Li
(74) *Attorney, Agent, or Firm* — Birch, Stewart, Kolasch & Birch, LLP

(57) ABSTRACT

Provided is a technique of predicting prognosis of skin cancer. A method for prognosis prediction of skin cancer includes: a step of obtaining a correlation amount correlated with an expression level of a glucose-6-phosphate dehydrogenase in a sample collected from a patient with the skin cancer; and a step of determining that the prognosis of the skin cancer is poorer when the correlation amount is large than that when the correlation amount is small.

11 Claims, 11 Drawing Sheets

P=0.0361 (Log-rank test)

- - ·  G6PD:low

──┴── G6PD:high

Fig.4

Comparative Example

Fig.5

Comparative Example r=0.068, CI[-0.19 to 0.31], P=0.59

Fig.12

| Case A | Case B | Case C |

METHOD FOR PROGNOSIS PREDICTION OF SKIN CANCER AND USE THEREOF

TECHNICAL FIELD

The present disclosure relates to a method for prognosis prediction of skin cancer. The present application is based on Japanese Patent Application No. 2020-072636 filed on Apr. 15, 2020, the contents of which are incorporated herein by reference.

BACKGROUND ART

In recent years, in various cancers including malignant melanoma, anti-malignant tumor treatment, through immune checkpoint inhibition, including an inhibitor of PD-L1 (programmed cell death ligand 1) and its receptor PD-1 (programmed cell death 1) has produced excellent results. Clinical use of anti-PD-L1 antibody drugs has started also for Merkel cell carcinoma, which is a type of skin cancer. PD-L1 expressed in tumor cells binds to PD-1 expressed in T cells, thereby inhibiting T cell activation and an immune reaction to assist tumor proliferation. Therefore, high expression of PD-L1 is known to indicate a poor prognosis in many cancers. However, high expression of PD-L1 is known to suggest a good prognosis of Merkel cell carcinoma (for example, Non Patent Literature 1).

In addition, PD-L1 is known to have heterogeneity even in the same case, and the present inventor has found and reported, for the first time, that PD-L1 has such heterogeneity also in Merkel cell carcinoma (Non Patent Literature 2). In addition, the present inventor has found and reported, for the first time, that there is no correlation between an expression level of PD-L1 in a primary lesion of Merkel cell carcinoma and prognosis, and that there is a strong correlation between an expression level of PD-L1 in a skin metastatic lesion of Merkel cell carcinoma and prognosis (Non Patent Literature 3).

CITATION LIST

Non Patent Literature

[NPL 1] Lipson E J, et al., Cancer Immunol. Res., 54-63, 2013
[NPL 2] Nakamura M. et al., Br J Dermatol., 1228-1229, 2019
[NPL 3] Nakamura M. et al., J Dermatol. Sci., 165-167, 2020

SUMMARY OF INVENTION

Technical Problem

According to Non Patent Literature 2, the expression level of PD-L1 greatly varies depending on the timing of excision and the difference in site, even in the same case. Therefore, it is difficult to predict the prognosis of Merkel cell carcinoma using PD-L1. In addition, according to Non Patent Literature 3, there is a strong correlation between the expression level of PD-L1 in a skin metastatic lesion of Merkel cell carcinoma and the prognosis, but it is difficult to use PD-L1 clinically as a prognostic predictor since the prognosis can be estimated for the first time after skin metastasis is observed. For this reason, other methods capable of predicting the prognosis of Merkel cell carcinoma have been desired. Such a problem has been a common problem not only in Merkel cell carcinoma but also in other skin cancers.

Solution to Problem

The present invention can be realized in the following forms.

(1) According to one form of the present invention, there is provided a method for prognosis prediction of skin cancer. The method for prognosis prediction of skin cancer of this form includes: a step of obtaining a correlation amount correlated with an expression level of a glucose-6-phosphate dehydrogenase in a sample collected from a patient with the skin cancer; and a step of determining that prognosis of the skin cancer is poorer when the correlation amount is large than that when the correlation amount is small. According to the method for prognosis prediction of skin cancer of this form, prognosis of the skin cancer can be predicted using, as an index, the expression level of the glucose-6-phosphate dehydrogenase in the sample collected from the patient with the skin cancer.

(2) In the method for prognosis prediction of skin cancer of the above form, the skin cancer may be at least one selected from the group consisting of Merkel cell carcinoma, malignant melanoma, squamous cell carcinoma, extramammary Paget disease, and cutaneous angiosarcoma.

(3) In the method for prognosis prediction of skin cancer of the above form, the skin cancer may include the Merkel cell carcinoma.

(4) In the method for prognosis prediction of skin cancer of the above form, the step of obtaining the correlation amount may include a step of obtaining the expression level of the glucose-6-phosphate dehydrogenase by immunohistostaining of the sample. According to the method for prognosis prediction of skin cancer of this form, the prognosis of the skin cancer can be easily predicted by performing the immunohistostaining on the sample collected from the patient with the skin cancer to obtain the expression level of the glucose-6-phosphate dehydrogenase.

(5) In the method for prognosis prediction of skin cancer according to the above form, the step of obtaining the correlation amount may include a step of obtaining an expression level of mRNA encoding the glucose-6-phosphate dehydrogenase in the sample. According to the method for prognosis prediction of skin cancer of this form, the prognosis of the skin cancer can be easily predicted by obtaining the expression level of the mRNA encoding the glucose-6-phosphate dehydrogenase in the sample collected from the patient with the skin cancer.

(6) In the method for prognosis prediction of skin cancer according to the above form, the step of obtaining the correlation amount may include a step of measuring activity of the glucose-6-phosphate dehydrogenase in blood or serum as the sample. According to the method for prognosis prediction of skin cancer of this form, the prognosis of the skin cancer can be easily predicted by measuring the activity of the glucose-6-phosphate dehydrogenase in blood or serum as the sample collected from the patient with the skin cancer.

(7) According to another form of the present invention, there is provided an evaluation method for evaluating effectiveness of an immune checkpoint inhibitor against skin cancer. The evaluation method of this form includes: a step of obtaining a correlation amount correlated with an expression level of a glucose-6-phosphate dehydrogenase in a sample collected from a patient with the skin cancer; and a step of evaluating that the effectiveness of the immune checkpoint inhibitor is higher when the correlation amount is small than that when the correlation amount is large. According to the evaluation method of this form, the effectiveness of the immune checkpoint inhibitor can be evaluated using, as an index, the expression level of the glucose-6-phosphate dehydrogenase in the sample collected from the patient with the skin cancer.

(8) According to another form of the present invention, there is provided a method for determining whether the immune checkpoint inhibitor can be administered to the patient of the skin cancer. The method of this form includes the evaluation method for evaluating effectiveness of an immune checkpoint inhibitor against skin cancer, and includes a step of determining to administer or continue administering the immune checkpoint inhibitor to the patient when the effectiveness of the immune checkpoint inhibitor is evaluated to be high. According to the method of this form, whether the immune checkpoint inhibitor can be administered can be determined using, as an index, the expression level of the glucose-6-phosphate dehydrogenase in the sample collected from the patient with the skin cancer.

(9) According to another form of the present invention, there is provided a method for evaluating malignancy of skin cancer. The method for evaluating malignancy of skin cancer of this form includes: a step of obtaining a correlation amount correlated with an expression level of a glucose-6-phosphate dehydrogenase in a sample collected from a patient with the skin cancer; and a step of determining that the malignancy of the skin cancer is higher when the correlation amount is large than that when the correlation amount is small. According to the method for evaluating malignancy of this form, the malignancy of the skin cancer can be evaluated using, as an index, the expression level of the glucose-6-phosphate dehydrogenase in the sample collected from the patient with the skin cancer.

(10) According to another form of the present invention, there is provided a biomarker for predicting prognosis of skin cancer. The biomarker of this form contains a glucose-6-phosphate dehydrogenase in a sample collected from a patient with the skin cancer, and indicates that, when an expression level of the biomarker in the sample is high, the prognosis of the skin cancer is poorer than that when the expression level is low.

(11) According to another form of the present invention, there is provided a biomarker for evaluating effectiveness of an immune checkpoint inhibitor against skin cancer. The biomarker of this form contains a glucose-6-phosphate dehydrogenase in a sample collected from a patient with the skin cancer, and indicates that, when the expression level of the biomarker in the sample is low, the effectiveness of the immune checkpoint inhibitor is higher than that when the expression level is high.

(12) According to another form of the present invention, there is provided a biomarker for evaluating malignancy of skin cancer. The biomarker of this form contains a glucose-6-phosphate dehydrogenase in a sample collected from a patient with the skin cancer, and indicates that, when an expression level of the biomarker in the sample is high, the malignancy of the skin cancer is higher than that when the expression level is low.

(13) According to another form of the present invention, there is provided a biomarker for predicting recurrence of skin cancer. The biomarker of this form contains a glucose-6-phosphate dehydrogenase in a sample collected from a patient suffering from the skin cancer, and indicates that, when an expression level of the biomarker in the sample is high, a possibility of the recurrence of the skin cancer is higher than that when the expression level is low.

(14) According to another form of the present invention, there is provided a method for predicting a possibility of onset of Grade≥3 immune-related adverse events resulting from administration of an immune checkpoint inhibitor to a patient with skin cancer. The method of this form includes a step of evaluating that the possibility of the onset of the Grade≥3 immune-related adverse events resulting from the administration of the immune checkpoint inhibitor is high when the effectiveness of the immune checkpoint inhibitor is evaluated to be high. According to the method of this form, the possibility of the onset of the Grade≥3 immune-related adverse events resulting from the administration of the immune checkpoint inhibitor can be predicted using, as an index, the expression level of the glucose-6-phosphate dehydrogenase in the sample collected from the patient with the skin cancer.

(15) According to another form of the present invention, there is provided a biomarker for predicting a possibility of onset of Grade≥3 immune-related adverse events resulting from administration of an immune checkpoint inhibitor against skin cancer. The biomarker of this form contains a glucose-6-phosphate dehydrogenase in a sample collected from a patient with the skin cancer, and indicates that, when the expression level of the biomarker in the sample is low, the possibility of the onset of the Grade≥3 immune-related adverse events resulting from the administration of the immune checkpoint inhibitor is higher than that when the expression level is high.

(16) According to another form of the present invention, there is provided a measurement kit. The measurement kit of this form is used in at least one of prognosis prediction of skin cancer, evaluation of effectiveness of an immune checkpoint inhibitor against the skin cancer, evaluation of malignancy of the skin cancer, prediction of recurrence of the skin cancer, prediction of a possibility of onset of Grade≥3 immune-related adverse events resulting from administration of the immune checkpoint inhibitor, and evaluation of an immune activity of the skin cancer. The measurement kit includes a substance capable of detecting a correlation amount correlated with an expression level of a glucose-6-phosphate dehydrogenase in a sample collected from a patient with the skin cancer. According to the measurement kit of this form, it is possible to easily detect the correlation amount correlated with the expression level of glucose-6-phosphate dehydrogenase in the sample collected from the patient with the skin cancer.

(17) In the measuring kit of this form, the substance capable of detecting the correlation amount may include at least one selected from the group consisting of a substance capable of binding to the glucose-6-phosphate dehydrogenase or a fragment thereof, a substance capable of binding to a gene encoding the glucose-6-phosphate dehydrogenase, and glucose-6 phosphate.

BRIEF DESCRIPTION OF DRAWINGS

FIG. 4 A view showing a Kaplan-Meier curve of an expression level of PD-Li.

FIG. 5 A view showing a result of correlation analysis of the expression level of PD-L1.

FIG. 12 An explanatory view showing a result of analysis of expression of G6PD by immunohistostaining in cutaneous angiosarcoma.

DESCRIPTION OF EMBODIMENTS

Figure 1:
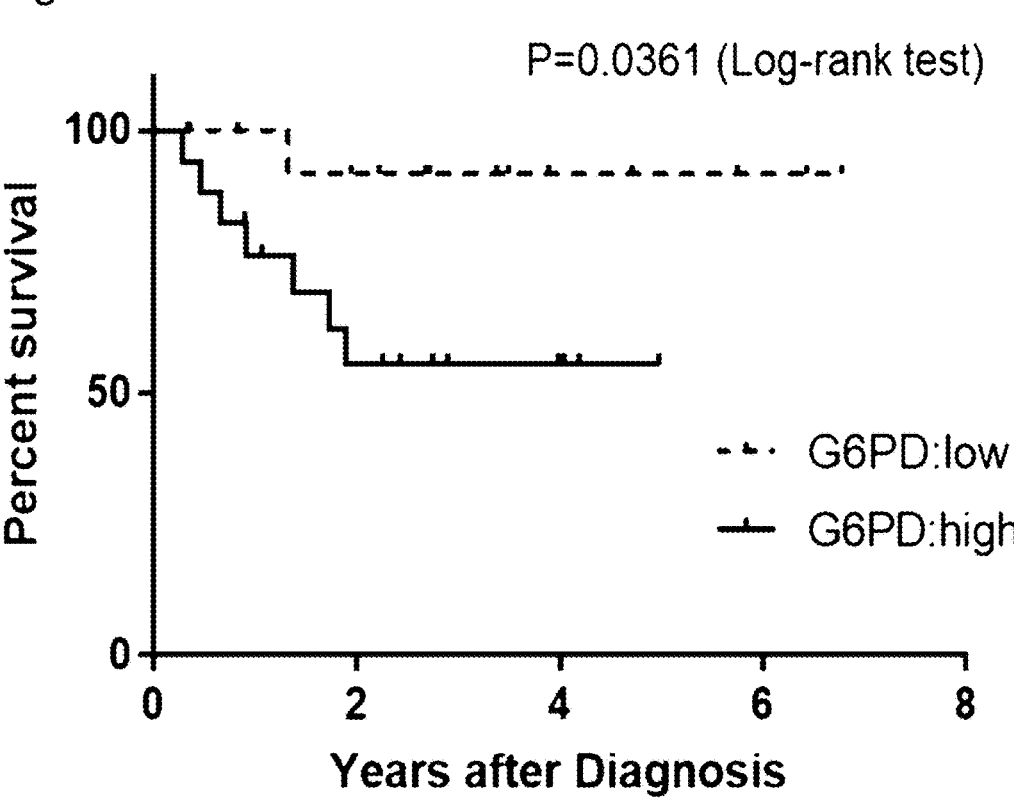
FIG. 1 A view showing a Kaplan-Meier curve of an mRNA expression level of G6PD.

According to one embodiment of the present disclosure, there is provided a method for prognosis prediction of skin cancer. The type of skin cancer is not particularly limited, and examples thereof include Merkel cell carcinoma, malignant melanoma, squamous cell carcinoma, extramammary Paget disease, and cutaneous angiosarcoma. A patient with skin cancer may be a patient with multiple concurrent skin cancers, and may be a patient either before treatment or after treatment. More specifically, the patient with skin cancer may be a patient either before surgery or after surgery, may be a patient either before immunotherapy or after immunotherapy, may be a patient either before chemotherapy or after chemotherapy, or may be a patient either before radiation therapy or after radiation therapy. In addition, the sex and age of the patient with skin cancer are not particularly limited. The animal species of the patient in the present embodiment is mainly a mammal. The mammal is not particularly limited, and examples thereof include primates such as humans and chimpanzees, dogs, cats, and rabbits.

As shown in the Examples which will be described later, the present inventor has found that, when the expression level of glucose-6-phosphate dehydrogenase is high in skin cancer, the prognosis tends to be poorer than that when the expression level of such an enzyme is low.

The method for prognosis prediction of skin cancer in the present embodiment includes: (I) a step of obtaining a correlation amount correlated with an expression level of a glucose-6-phosphate dehydrogenase in a sample collected from a patient with the skin cancer (hereinafter also referred to as step (I)); and (II) a step of determining that prognosis of the skin cancer is poorer when the correlation amount is large than that when the correlation amount is small (hereinafter also referred to as step (II)).

As the sample used in the step (I), tissue in which carcinoma is present separated from the patient with the skin cancer, blood or serum collected from the patient with skin cancer, or the like can be used. The tissue is not particularly limited, and examples thereof include a formalin-fixed paraffin-embedded (FFPE) specimen, at least a part of a tumor resected by surgery or the like, and a sample containing a plurality of tissue constituting cells collected by biopsy or the like.

In the present embodiment, the glucose-6-phosphate dehydrogenase means an enzyme under the enzyme number EC1.1.1.49. The glucose-6-phosphate dehydrogenase (hereinafter, also referred to as "G6PD") oxidizes glucose-6 phosphate as a substrate in the presence of a coenzyme such as nicotinamide adenine dinucleotide (NAD) or nicotinamide adenine dinucleotide phosphate (NADP) to catalyze a reaction for producing glucono-1,5-lactone-6 phosphate and reduced NAD (NADH) or reduced NADP (NADPH), or a reverse reaction thereof.

In the present embodiment, the correlation amount correlated with the expression level of G6PD means a correlation amount having a positive correlation with the expression level of G6PD. The correlation amount is not particularly limited, and examples thereof include the expression level of G6PD itself, an expression level of mRNA encoding G6PD, and an activity of G6PD.

The expression level of G6PD can be obtained by, for example, a Western blotting method based on an antigen-antibody reaction using an anti-G6PD antibody or a fragment thereof, a dot blotting method, an immunoprecipitation method, an ELISA method, an immunohistostaining method, or the like. The expression level of mRNA encoding G6PD can be obtained by, for example, a next generation sequence analysis method, a Northern hybridization method, a dot hybridization method, RT-PCR, real-time PCR, or the like. The activity of G6PD can be measured using, for example, a kit for measuring the G6PD activity using glucose-6 phosphate as a substrate. Obtaining the expression level of G6PD by an immunostaining method has little variation in cases, and is excellent as a biomarker. In addition, obtaining the expression level of G6PD by a serum test using serum is suitable for monitoring because of high sensitivity.

In the step (II), for example, (i) when the expression level of G6PD or the expression level of mRNA encoding G6PD is high, it may be determined that the prognosis of skin cancer is poorer than that when the expression level is low, and (ii) when the activity of G6PD is high, it may be determined that the prognosis of skin cancer is poorer than that when the activity of G6PD is low. The magnitudes of the expression level and the activity may be determined by comparison with a predetermined reference value, or may be determined by comparison between values in samples collected at different timings in the same patient. In the present embodiment, the "poor prognosis" means that the malignancy of skin cancer is high and that a disease state thereof tends to deteriorate. That is, when the prognosis is poor, there is a possibility of metastasis or recurrence.

For example, in a case where the expression level of G6PD is high in a resected specimen as the sample, it is considered to be a high risk group with a high malignancy of skin cancer, and postoperative radiation therapy or the like may be added. Also, for example, in a case where the expression level of G6PD is low in a resected specimen as the sample, it is considered to be a low risk group with a low malignancy of skin cancer, and a follow-up observation may be performed while the addition of postoperative radiation therapy or the like may be suspended. As described above, the method for prognosis prediction of skin cancer in the present embodiment can be used as a method for assisting determination of a treatment policy for skin cancer. The method for prognosis prediction of skin cancer can be rephrased as a method for predicting prognosis of skin cancer.

According to another embodiment of the present disclosure, there is provided an evaluation method for evaluating effectiveness of an immune checkpoint inhibitor against skin cancer. In the present embodiment, the immune checkpoint inhibitor means a drug that inhibits signal transduction by an immune checkpoint by inhibiting binding between the immune checkpoint and its ligand. Examples of the immune checkpoint inhibitor include an anti-PD-L1 antibody drug and an anti-PD-1 antibody drug. The anti-PD-L1 antibody drug is composed of a human-type monoclonal antibody, and binds to PD-L1 (programmed cell death ligand 1) expressed in tumor cells, thereby inhibiting PD-L1 from binding to PD-1 (programmed cell death 1) expressed in T cells and maintaining activation of the T cells. By binding to PD-1, the anti-PD-1 antibody drug inhibits PD-L1 from binding to PD-1 and maintains activation of T cells.

As shown in the Examples which will be described later, the inventor of the present invention has found that the expression level of G6PD shows an inverse correlation with PD-L 1 in skin cancer, and that the expression level of PD-L1 decreases as the expression level of G6PD increases. It can be said that the higher the expression level of G6PD, that is, the lower an estimated expression level of PD-L1, the higher the possibility that the tumor may have low immunological activity.

In the present embodiment, an evaluation method for evaluating effectiveness of an immune checkpoint inhibitor against skin cancer includes: the above step (I), i.e., the step of obtaining a correlation amount correlated with an expression level of a glucose-6-phosphate dehydrogenase in a sample collected from a patient with the skin cancer; and (III) a step of evaluating that the effectiveness of the immune checkpoint inhibitor is higher when the correlation amount is small than that when the correlation amount is large (hereinafter also referred to as step (III)).

In the step (III), for example, (i) when the expression level of G6PD or the expression level of mRNA encoding G6PD is low, it may be determined that the effectiveness of the immune checkpoint inhibitor is higher than that when the expression level is high, and (ii) when the activity of G6PD is low, it may be evaluated that the effectiveness of the immune checkpoint inhibitor is higher than that when the activity of G6PD is high. The magnitudes of the expression level and the activity may be determined by comparison with a predetermined reference value, or may be determined by comparison between values in samples collected at different timings in the same patient.

In consideration of a mechanism of the immune checkpoint inhibitor such as an anti-PD-L1 antibody drug, it is presumed that the effect of the immune checkpoint inhibitor such as an anti-PD-L1 antibody drug is low when the expression level of PD-L1 is low, and that the effect of the immune checkpoint inhibitor such as an anti-PD-L1 antibody drug is high when the expression level of PD-L1 is high. Therefore, in the above step (III), when the expression level of G6PD is low, that is, it is presumed by the correlation between G6PD and PD-L1 that the expression level of PD-L1 is high, the effectiveness of the immune checkpoint inhibitor such as an anti-PD-L1 antibody drug is evaluated to be higher than that when the expression level of G6PD is high, that is, it is presumed by the correlation between G6PD and PD-L1 that the expression level of PD-L1 is low.

For example, when the expression level of G6PD in the sample is small and the expression level of PD-L1 is small, it is expected that the expression level of PD-L1 temporarily decreases due to heterogeneity of PD-L1. Even in such a case, the effectiveness of the immune checkpoint inhibitor such as an anti-PD-L1 antibody drug may be evaluated to be high since the expression level of G6PD is low. G6PD has a small variation in numerical value in the same case, and thus is superior to PD-L1 having a large variation in numerical value in the same case as an evaluation index of effectiveness or the like of the immune checkpoint inhibitor. The evaluation method for evaluating effectiveness of an immune checkpoint inhibitor against skin cancer in the present embodiment can be used as a method for assisting determination of a treatment policy for skin cancer, such as determination regarding administration of an immune checkpoint inhibitor.

According to another embodiment of the present disclosure, there is provided a method for determining whether the immune checkpoint inhibitor can be administered to the patient of the skin cancer. The method includes (IV) a step of determining to administer or continue administering the immune checkpoint inhibitor to the patient when the effectiveness of the immune checkpoint inhibitor is evaluated to be high (hereinafter, also referred to as step (IV)), in the step (III) of the evaluation method for evaluating effectiveness of an immune checkpoint inhibitor against skin cancer.

In the step (IV), it may be determined that the immune checkpoint inhibitor is newly administered to a patient to whom the immune checkpoint inhibitor has not been administered, or it may be determined that administration of the immune checkpoint inhibitor is continued to a patient to whom the immune checkpoint inhibitor has already been administered.

For example, in a case where the expression level of G6PD in the sample is high and the expression level of PD-L1 is low, the effect of the immune checkpoint inhibitor such as an anti-PD-L1 antibody drug is evaluated to be low, and thus a surgical therapy such as lymphadenectomy may be selected instead of the administration of the immune checkpoint inhibitor. In addition, for example, in a case where a blood G6PD value is maintained low upon administration of the immune checkpoint inhibitor such as an anti-PD-L1 antibody drug, the effectiveness of the immune checkpoint inhibitor is evaluated to be high, and thus the administration of the immune checkpoint inhibitor may be continued. In addition, for example, in a case where the blood G6PD value tends to increase after the administration of the immune checkpoint inhibitor, the effectiveness of the immune checkpoint inhibitor is evaluated to be low, and thus an additional treatment such as radiation therapy may be considered. In addition, for example, when the expression level of G6PD in the sample is low and the estimated expression level of PD-L1 is high, the tumor is considered to have a high immune activity, and thus the immune checkpoint inhibitor may be introduced with careful attention to side effects.

As described above, the present inventor has found that the higher the expression level of G6PD, that is, the lower the estimated expression level of PD-L1, the higher the possibility that the tumor may have low immunological activity. From this, the immune activity of skin cancer can be evaluated using the expression level of G6PD as an index. That is, as another embodiment of the present disclosure, an evaluation method for an immune activity of skin cancer is provided. The evaluation method includes: a step of obtaining a correlation amount correlated with an expression level of G6PD in a sample collected from a patient with skin cancer; and a step of determining that the immune activity of the skin cancer is higher when the correlation amount is large than that when the correlation amount is small.

According to another embodiment of the present disclosure, a biomarker is provided. This biomarker contains G6PD in a sample collected from a patient with skin cancer. Such a biomarker can be used for predicting prognosis of skin cancer, for evaluating effectiveness of an immune checkpoint inhibitor for skin cancer, for evaluating malignancy of skin cancer, and for predicting recurrence of skin cancer. In addition, such a biomarker can be used for predicting a possibility of onset of Grade≥3 immune-related adverse events resulting from administration of an immune checkpoint inhibitor against skin cancer, or for evaluating an immune activity of skin cancer. Furthermore, according to the present disclosure, G6PD in a sample collected from a patient with skin cancer is assumed to be used as a biomarker. More specifically, G6PD in a sample collected from a patient with skin cancer, which is used in at least one of prognosis prediction of skin cancer, evaluation of effectiveness of an immune checkpoint inhibitor against the skin cancer, evaluation of malignancy of the skin cancer, prediction of recurrence of the skin cancer, prediction of a possibility of onset of Grade≥3 immune-related adverse events resulting from administration of the immune checkpoint inhibitor, and evaluation of an immune activity of the skin cancer, is assumed to be used as a biomarker.

The biomarker for predicting prognosis of skin cancer indicates that, when the expression level of the biomarker is high, the prognosis of skin cancer is poorer than that when the expression level is low. The biomarker for evaluating effectiveness of an immune checkpoint inhibitor against skin cancer indicates that, when the expression level of the biomarker is high, the effectiveness of the immune checkpoint inhibitor is higher than that when the expression level is low. The biomarker for evaluating malignancy of skin cancer indicates that, when the expression level of the biomarker is high, the malignancy of skin cancer is higher than that when the expression level is low.

The biomarker for predicting recurrence of skin cancer indicates that, when the expression level of the biomarker in a sample collected from a patient suffering from skin cancer is high, the possibility of recurrence of skin cancer is higher than that when the expression level is low. For example, when the blood G6PD value increases during postoperative course observation, the possibility of recurrence of skin cancer is assumed, and thus image examination may be performed.

The biomarker for evaluating an immune activity of skin cancer indicates that, when the expression level of the biomarker in a sample collected from a patient suffering from skin cancer is high, the immune activity of the skin cancer is higher than that when the expression level is low.

The biomarker for predicting a possibility of onset of Grade≥3 immune-related adverse events (irAEs) resulting from administration of an immune checkpoint inhibitor against skin cancer indicates that, when the expression level of the biomarker in a sample collected from a patient with skin cancer is low, the possibility of the onset of the Grade≥3 irAEs resulting from the administration of the immune checkpoint inhibitor is higher than that when the expression level is high. This is supported by the fact that, when the expression level of G6PD is low, a frequency of onset of a severe irAE resulting from the administration of the immune checkpoint inhibitor is higher than that when the expression level of G6PD is high, as shown in the Examples which will be described later.

According to another form of the present disclosure, there is provided a method for predicting a possibility of onset of Grade≥3 immune-related adverse events (irAEs) resulting from administration of an immune checkpoint inhibitor to a patient with skin cancer. This method includes (V) a step of evaluating that the possibility of the onset of the Grade≥3 irAEs resulting from the administration of the immune checkpoint inhibitor is high (hereinafter, also referred to as step (V)), when the effectiveness of the immune checkpoint inhibitor is evaluated to be high in the step (III) of the evaluation method for evaluating effectiveness of an immune checkpoint inhibitor against skin cancer. In addition, the method for predicting a possibility of onset of Grade≥3 irAEs resulting from administration of an immune checkpoint inhibitor to a patient with skin cancer may be a method including the above step (I), that is, (I) the step of obtaining a correlation amount correlated with an expression level of G6PD in a sample collected from a patient with skin cancer, and (VI) a step of evaluating that, when the correlation amount is small, the possibility of the onset of the Grade≥3 irAEs resulting from the administration of the immune checkpoint inhibitor is higher than that when the correlation amount is large (hereinafter, also referred to as step (VI)).

For example, when the expression level of G6PD in the sample is low and the estimated expression level of PD-L1 is high, it is considered that the tumor has a high immune activity, and thus there is a high possibility that the effectiveness of the immune checkpoint inhibitor may be high. In such a tumor having a high immune activity, there is a high possibility of the onset of the Grade≥3 irAEs resulting from the administration of the immune checkpoint inhibitor, and thus it is assumed that sufficient attention is paid to the irAE in the administration of the immune checkpoint inhibitor. As described above, the method for predicting a possibility of onset of Grade≥3 irAEs resulting from administration of an immune checkpoint inhibitor to a patient with skin cancer in the present embodiment can be used as a method for assisting determination of a treatment policy for skin cancer, such as determination regarding administration of an immune checkpoint inhibitor.

According to another form of the present disclosure, there is provided a measurement kit. This measurement kit is used in at least one of prognosis prediction of skin cancer, evaluation of effectiveness of an immune checkpoint inhibitor against the skin cancer, evaluation of malignancy of the skin cancer, prediction of recurrence of the skin cancer, prediction of a possibility of onset of Grade≥3 immune-related adverse events resulting from administration of the immune checkpoint inhibitor, and evaluation of an immune activity of the skin cancer. The measurement kit includes a substance capable of detecting a correlation amount correlated with an expression level of G6PD in a sample collected from a patient with the skin cancer. In other words, the measurement kit includes a companion diagnostic agent that can be used in companion diagnosis of the skin cancer. The substance capable of detecting the correlation amount correlated with the expression level of G6PD may include at least one selected from the group consisting of a substance capable of binding to G6PD or a fragment of G6PD, a substance capable of binding to a gene encoding G6PD, and glucose-6 phosphate.

Examples of the substance capable of binding to G6PD or a fragment of G6PD include an anti-G6PD antibody and a fragment thereof. Examples of the substance capable of binding to the gene encoding G6PD include a primer set capable of amplifying the gene of G6PD, and a probe that specifically hybridizes to the gene of G6PD. The glucose-6 phosphate may be included in the measurement kit as a substrate for measuring the activity of G6PD.

The form of the measurement kit is not particularly limited, and may be, for example, a dry state or a state in which the substance capable of detecting the correlation amount correlated with the expression level of G6PD is dissolved in a solution. In addition, the substance may be labeled with, for example, a labeling substance such as a secondary antibody, a fluorescent substance, or a radioisotope, or may be in a state of being immobilized on a base material of a microarray, a microtiter plate, or a support such as resin or metal beads. In addition to the above substances, the measurement kit may include various components such as reverse transcriptase, DNA polymerase, dNTP, oligo dT primer, random primer, RNase inhibitor, RNase H, labeling substance, and buffer solution. Furthermore, the measurement kit may include various devices that can be used to obtain the expression level of G6PD, instructions for use, and the like.

EXAMPLES

Hereinafter, the present invention will be described more specifically with reference to Examples, but is not limited to the following Examples.

<Merkel Cell Carcinoma>

1. Sample

Formalin-fixed paraffin-embedded (FFPE) specimens and sera in cases of Merkel cell carcinoma on which histopathological examination had been performed so that the postoperative course for a certain period of time had been clarified were used as samples. There were used 90 FFPE specimens of 71 cases and 50 serum specimens of 19 cases. Patients as the cases of the FFPE specimens had an age of 40 to 98 years, a mean age of 77.27 years, and a male:female ratio of 26:45. Tumor sites in these cases were head and neck: 66.2% (face: 42 cases; neck: 2 cases, ear: 1 case, and head: 2 cases), extremities: 29.6% (upper arm: 4 cases, forearm: 3 cases, finger: 3 cases, thigh: 6 cases, lower leg: 3 cases, and foot: 2 cases), and trunk: 2.8% (buttocks: 2 cases). Among them, 6 cases regressed spontaneously.

2. Search for Biomarker Correlated with PD-L1

2-1. Extraction of RNA
From unstained slides prepared from the FFPE specimens, the tumor part and the surrounding inflammatory cell infiltration part were macrodissected using a 18 G needle, and RNA was extracted using AllPrep DNA/RNA FFPE Kit (manufactured by Qiagen). When the RIN value and DV200 (median of RNA fragment size) were measured using a bioanalyzer (Agilent 2100, manufactured by Agilent), 44 samples were selected from those having DV200 of 30% or more.
2-2. Next Generation Sequence Analysis
Next generation sequence analysis (NGS analysis) was performed on the 44 samples using Immune Response Panel (Ampliseq) on a MiniSeq (manufactured by Illumina) system. The obtained data was analyzed on BaseSpace (registered trademark) Sequence Hub (manufactured by Illumina).

When the group with high PD-L1 expression was compared with the group with low PD-L1 expression, only glucose-6-phosphate dehydrogenase (G6PD) had a q value (p-adjust) of 0.05 or less as a factor correlated with PD-L1. A low value of PD-L1 provided the result of a dominantly high G6PD value (p=0.00011, q=0.040). That is, it was found that G6PD has an inverse correlation with PD-L1.

3. Study on Presence or Absence of Correlation Between mRNA Expression Level of G6PD and Prognosis The presence or absence of a correlation between the mRNA expression level of G6PD and the presence or absence of metastasis during the course of patients suffering from skin cancer was examined. As a result, the mRNA expression level of G6PD correlated with the presence or absence of metastasis during the course of patients suffering from skin cancer. The cases where the mRNA expression level of G6PD was high showed a dominantly high rate of lymph node metastasis and distant metastasis observed during the course (p=0.00016, q=0.018). An ROC curve was drawn according to the presence or absence of metastasis, and a value of 1071 CPM (counts per million) or more calculated as a reference point was defined as high mRNA expression level of G6PD, and a value of 1071 CPM or less was defined as low mRNA expression level of G6PD.

FIG. 1 is a view showing a Kaplan-Meier curve of the mRNA expression level of G6PD. FIG. 1 shows a Kaplan-Meier curve for the survival rate of each of a group with a high mRNA expression level of G6PD and a group with a low mRNA expression level of G6PD. In FIG. 1, the group with a high mRNA expression level of G6PD is indicated by a solid line, and the group with a low mRNA expression level of G6PD is indicated by a broken line. In FIG. 1, the vertical axis represents the overall survival rate, the horizontal axis represents the number of years, and the P value represents the log-rank test value. As shown in FIG. 1, when the mRNA expression level of G6PD was high, there was observed a significant correlation with a lower survival rate, i.e., a poorer prognosis, than that when the mRNA expression level of G6PD was low (P=0.036).

4. Immunohistostaining 4-1. Immunohistostaining of G6PD
Immunohistostaining of G6PD was performed using slides made from the FFPE specimens. As the antibody, Anti-G6PD antibody (HPA000247, manufactured by Sigma-Ardrich) was used. Photographing and analysis were performed using all-in-one fluorescence microscope BZ-X 800 (manufactured by KEYENCE). Staining results were digitized, and positive cells and expression intensity were quantified and evaluated.

Figure 2:
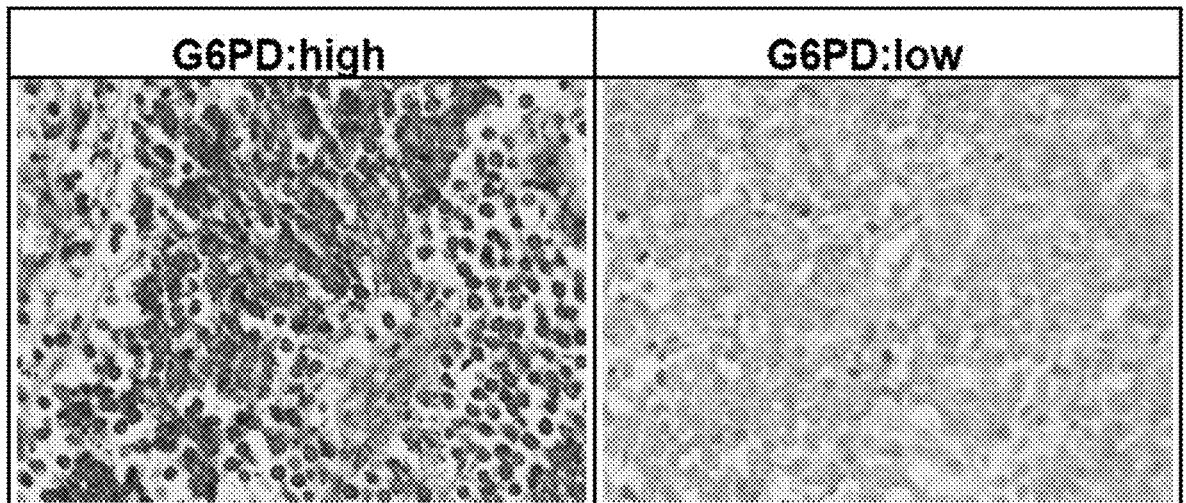
FIG. 2 An explanatory view showing a result of analysis of expression of G6PD by immunohistostaining.

FIG. 2 is an explanatory view showing a result of analysis of expression of G6PD by immunohistostaining. In FIG. 2, an example of an image of immunohistostaining in a group showing high G6PD expression is shown on the left side of the figure, and an example of an image of immunohistostaining in a group showing low G6PD expression is shown on the right side thereof. The expression level of G6PD in immunohistostaining was evaluated by visual observation of stained specimens under a microscope, and a staining rate of 50% or more was defined as high, and a staining rate of less than 50% was defined as low.

Figure 3:
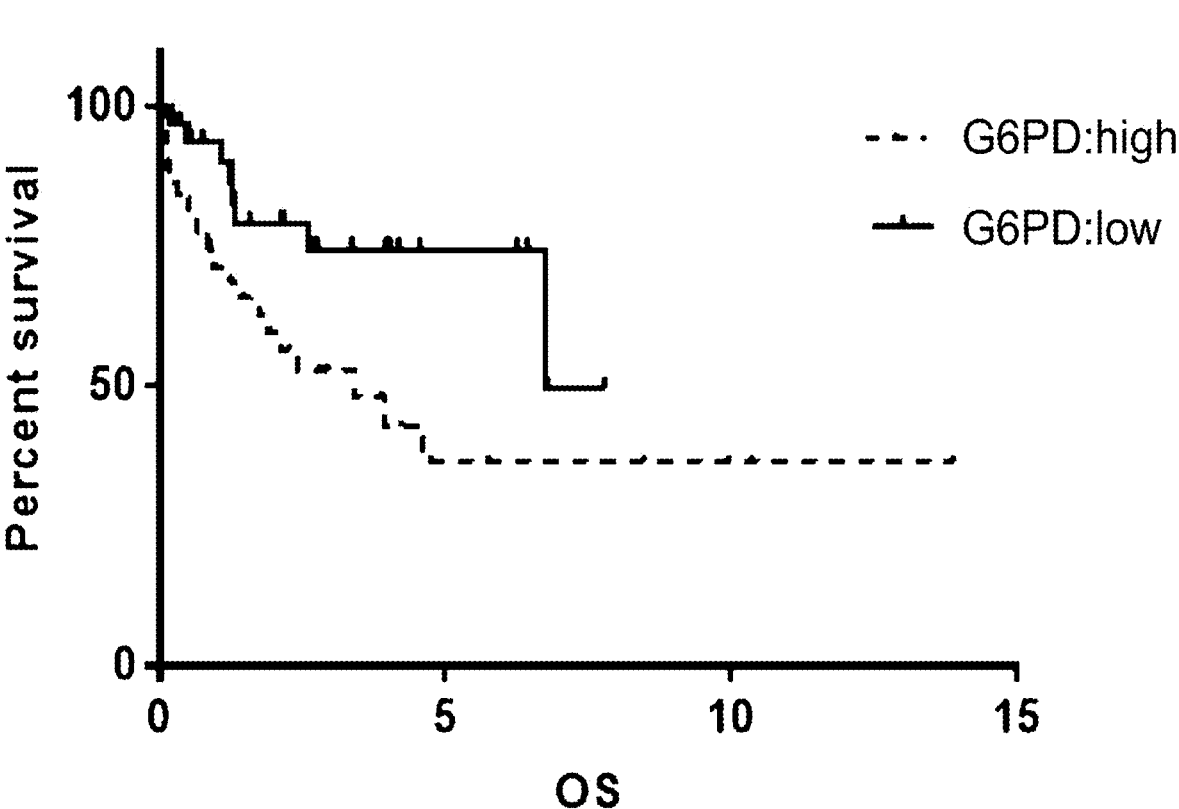
FIG. 3 A view showing a Kaplan-Meier curve of an expression level of G6PD.

FIG. 3 is a view showing a Kaplan-Meier curve of the expression level of G6PD. FIG. 3 shows a Kaplan-Meier curve for the survival rate of each of a group with a high expression level of G6PD and a group with a low expression level of G6PD. In FIG. 3, the group with a high expression level of G6PD is indicated by a broken line, and the group with a low expression level of G6PD is indicated by a solid line. In FIG. 3, the vertical axis represents the overall survival rate, and the horizontal axis represents the overall survival (OS). As shown in FIG. 3, when the expression level of G6PD was high, there was observed a significant correlation with a lower survival rate, i.e., a poorer prognosis than that when the expression level of G6PD was low (P=0.036).

4-2. Immunohistostaining of PD-L1 in Primary Lesion

As a comparative example, immunohistostaining of PD-L1 was performed using slides prepared from FFPE specimens in a primary lesion. As the antibody, Anti-PD-L1 antibody (28-8, ab205921, manufactured by Abcam) was used, and photographing and analysis were performed using all-in-one fluorescence microscope BZ-X 800 (manufactured by KEYENCE). Staining results were digitized, and positive cells and expression intensity were quantified and evaluated.

Figure 4:
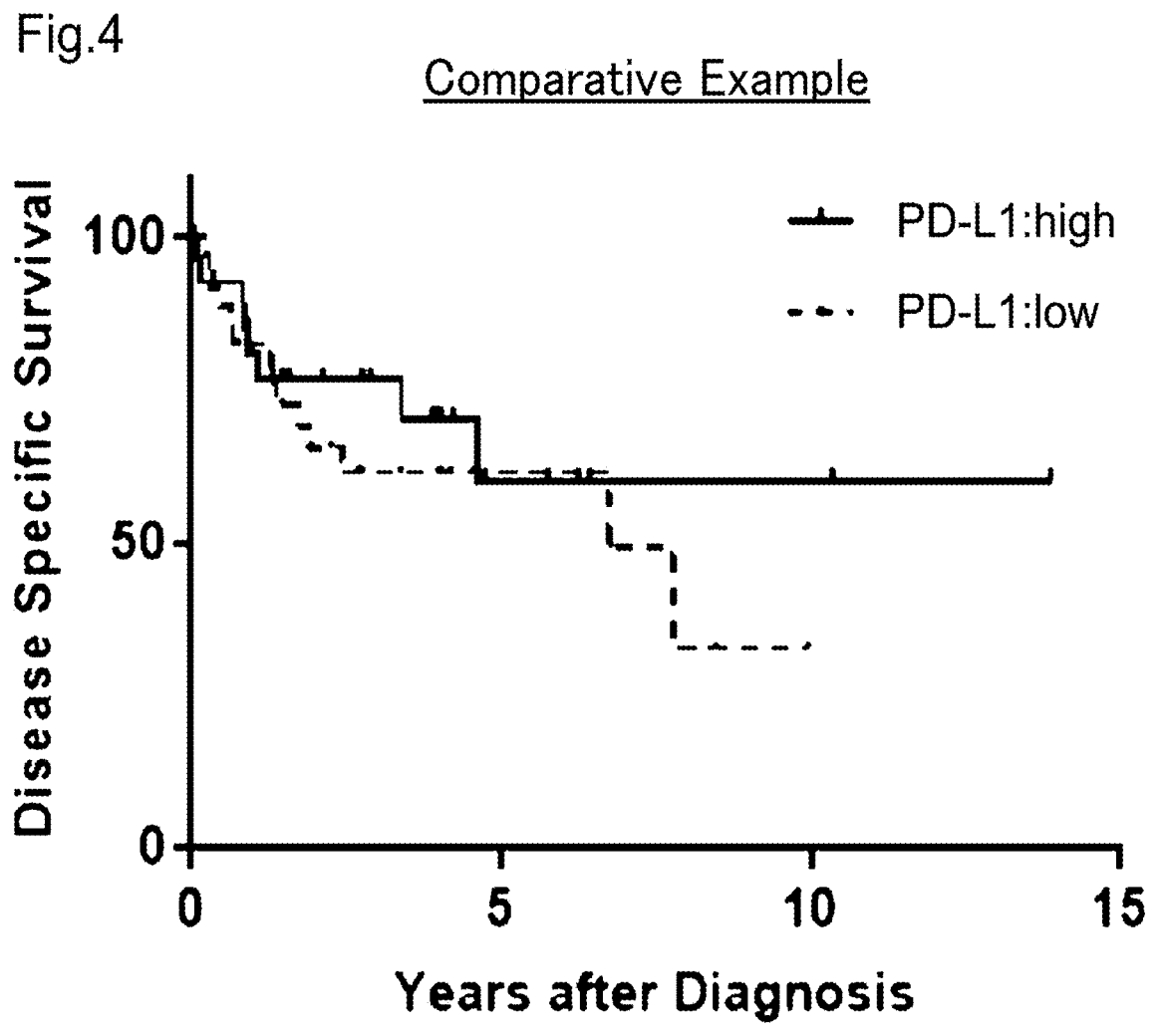
Figure 5:
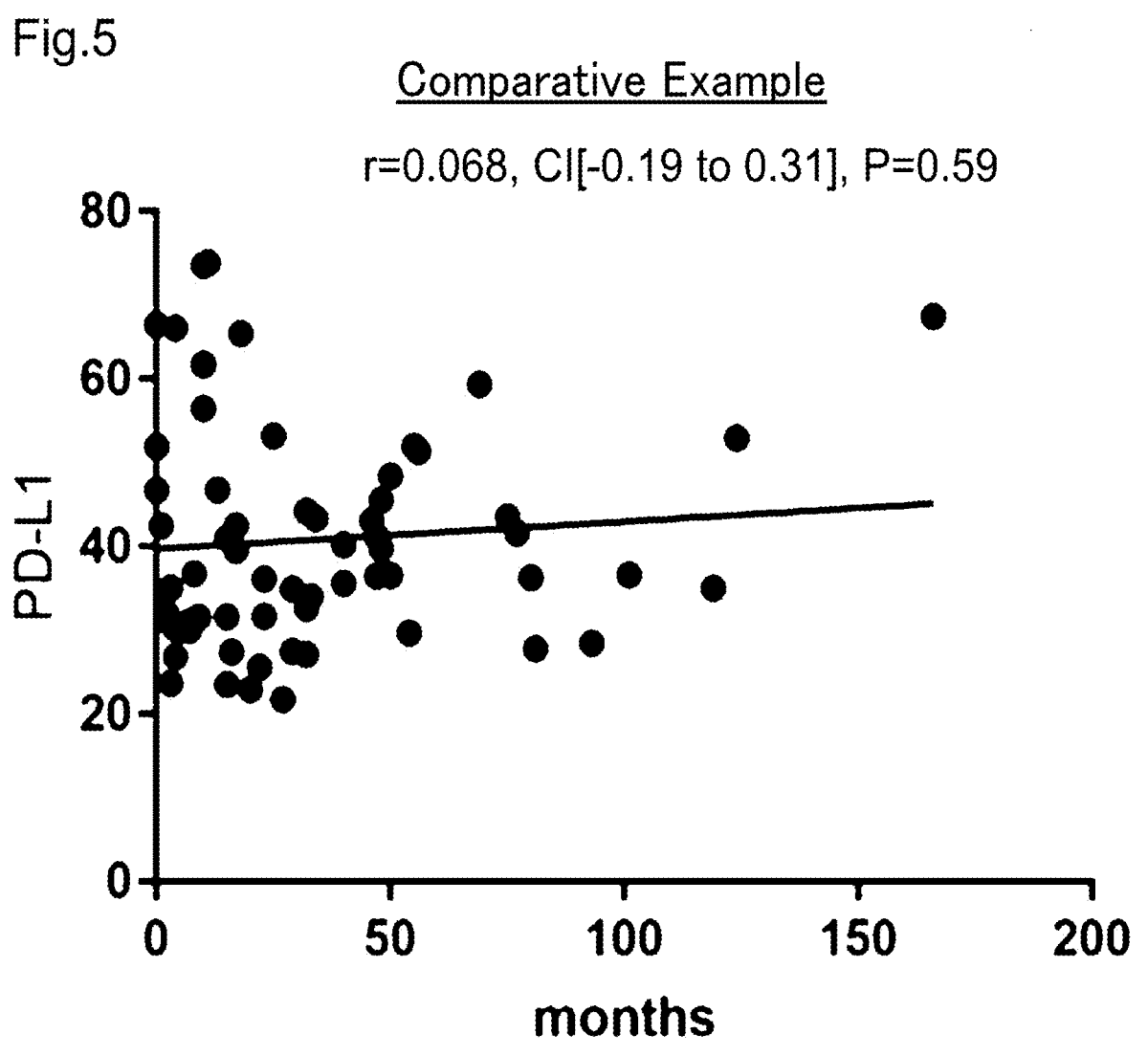

FIG. 4 is a view showing a Kaplan-Meier curve of the expression level of PD-L1. FIG. 5 is a view showing a result of correlation analysis of the expression level of PD-L1. FIG. 4 shows a Kaplan-Meier curve for the survival rate of each of a group with a high expression level of PD-L1 and a group with a low expression level of PD-L1. In FIG. 4, the group with a high expression level of PD-Li is indicated by a solid line, and the group with a low expression level of G6PD is indicated by a broken line. In FIG. 4, the vertical axis represents the overall survival rate, and the horizontal axis represents the number of years. In FIG. 5, the vertical axis represents the expression level (pixel value) of PD-L1, and the horizontal axis represents the number of months. As shown in FIGS. 4 and 5, in the comparison between the group showing high expression of PD-L1 and the group showing low expression of PD-L1, no correlation with the survival rate was observed (r=0.068, CI [−0.19 to 0.31], P=0.59).

4-3. Discussion of Immunohistostaining

From the results of immunohistostaining of G6PD and PD-L1, no correlation between the expression level of PD-L1 and the prognosis was observed, whereas a correlation between the expression level of G6PD and the prognosis was observed, indicating that G6PD can be used as a more excellent prognosis prediction marker than PD-L1.

5. G6PD Activity 5-1. Measurement of G6PD Activity Using Serum

For 50 patient serum specimens of 19 cases, the G6PD activity was measured using a G6PD assay kit (Abcam, ab102529). The average activity value of the 50 specimens was 11.45 mU/ml.

5-2. Relationship Between G6PD Activity and Course

Figure 6:
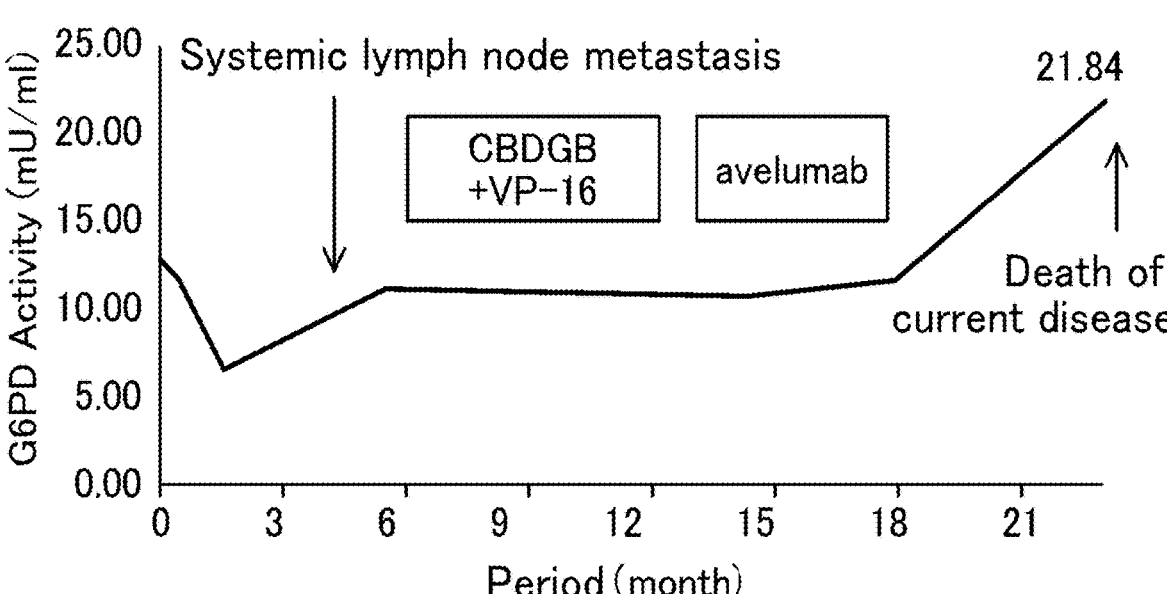
FIG. 6 An explanatory view showing transition of G6PD activity in Case 1.
Figure 7:
FIG. 7 An explanatory view showing transition of G6PD activity in Case 2.
Figure 8:
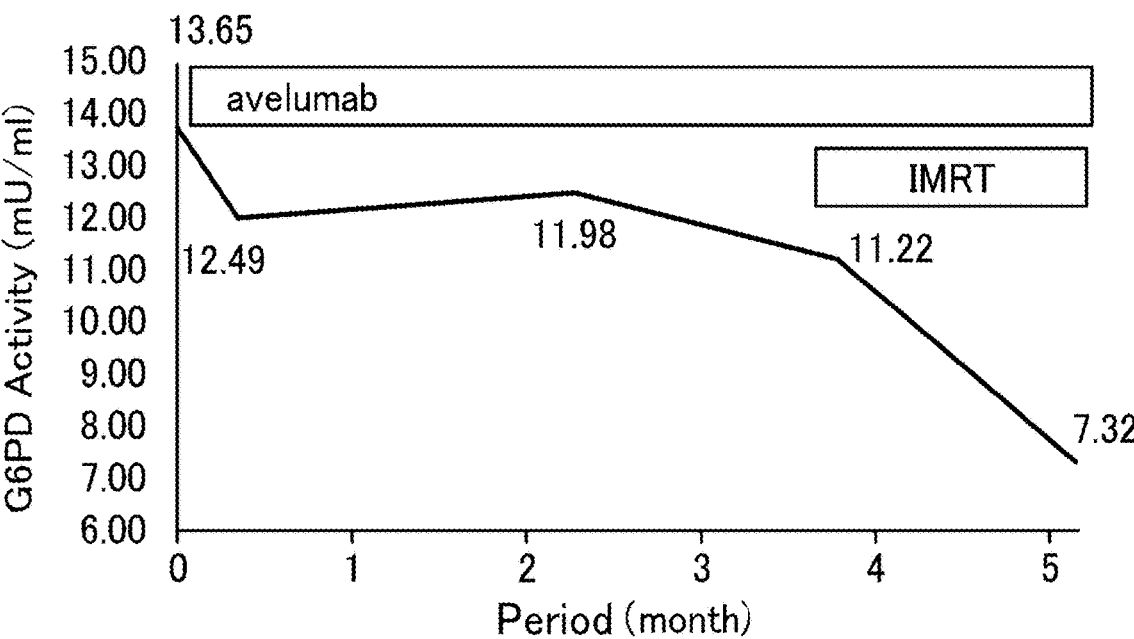
FIG. 8 An explanatory view showing transition of G6PD activity in Case 4.

The course of Merkel cell carcinoma was confirmed for the cases (Case 1 to 3) of 3 specimens having a particularly high G6PD activity (19 mU/ml or more) among the 50 specimens. In addition, the course of Merkel cell carcinoma was confirmed for a case (Case 4) having a decreased G6PD activity. In FIGS. 6 to 8 shown below, the vertical axis represents the G6PD activity (mU/ml), and the horizontal axis represents the period.

(1) Case 1

FIG. 6 is an explanatory view showing transition of the G6PD activity in Case 1.

Case 1 was a stage IV case, and the primary lesion was located in the right mandible. In Case 1, surgical resection and radiation therapy were performed, but systemic lymph node metastasis was observed about 9 months after the surgical resection. Thereafter, a combination therapy of CBDGB and VP-16 was performed, but no therapeutic effect was observed. Therefore, a trial of avelumab as an immune checkpoint inhibitor was performed, but death of current disease was caused after several months. A high G6PD activity was observed when the death of current disease was caused, and the G6PD activity was 21.84 mU/ml.

(2) Case 2

FIG. 7 is an explanatory view showing transition of the G6PD activity in Case 2. Case 2 was a stage IV case, and the primary lesion was located in the left lower leg. In Case 2, surgical resection, SLNB, and radiation therapy were performed, but local recurrence was observed about 1 year after the excision and skin grafting. A high G6PD activity was observed at the time of local recurrence, and the G6PD activity was 19.63 mU/ml.

(3) Case 3

Case 3 was a stage II case, and the primary lesion was located in the anterior chest. In Case 3, surgical resection and radiation therapy were performed, but death of other diseases was caused about 2 months after the end of the radiation therapy. A high G6PD activity was observed before the death of other diseases, and the G6PD activity was 19.37 mU/ml.

(4) Case 4

FIG. 8 is an explanatory view showing transition of the G6PD activity in Case 4. Case 4 was a stage III case, and the primary lesion was located in the nasal root. In Case 4, after surgical resection, appearance of accumulation in the right submandibular lymph node was observed by PET/CT, and, therefore, administration of avelumab as an immune checkpoint inhibitor was started. Since enhancement of the accumulation was observed by PET/CT after 3 months, IMRT (intensity-modulated radiation therapy) was used in combination, resulting in complete remission (CR). The G6PD activity was significantly reduced by the use of avelumab and IMRT in combination.

6. Conclusion

From the above results, it was found that, in Merkel cell carcinoma as skin cancer, the expression level of G6PD shows an inverse correlation with PD-L1, and that the expression level of PD-L1 decreases as the expression level of G6PD increases. In addition, when the expression level of G6PD was high, there was a correlation with a poorer prognosis than that when the expression level of G6PD was low. In addition, it was suggested that, when the G6PD activity in the serum is high and the expression level of G6PD is high, the possibility of recurrence of skin cancer is higher than that when the G6PD activity is low and the expression level of G6PD is low. In other words, it was suggested that, when the expression level of G6PD is high, the malignancy of skin cancer tends to be higher and the disease state tends to deteriorate as compared with when the expression level of G6PD is low. Therefore, G6PD was found to be effective as a biomarker for predicting prognosis of skin cancer, a biomarker for evaluating malignancy of skin cancer, and a biomarker for predicting recurrence of skin cancer. Therefore, it was found that, by using the expression level of G6PD as an index, the prognosis of skin cancer can be predicted, the effectiveness of the immune checkpoint inhibitor can be evaluated, whether the immune checkpoint inhibitor can be administered can be determined, and the malignancy of skin cancer can be evaluated. In addition, since the expression level of PD-L1 decreased as the expression level of G6PD increased, it was suggested that the immune activity of skin cancer can be evaluated using the expression level of G6PD as an index.

<Malignant Melanoma>

1. Sample

Samples of primary lesions in 30 cases of malignant melanoma that had undergone immune checkpoint treatment were used. The immune checkpoint treatment means that administration of an immune checkpoint inhibitor was performed. A method of extracting RNA, a method of next generation sequence analysis, a method of immunohistostaining of G6PD, evaluation criteria for the G6PD expression level, and the like are the same as those described in the Example of Merkel cell carcinoma.

2. Immunohistostaining

Figure 9:
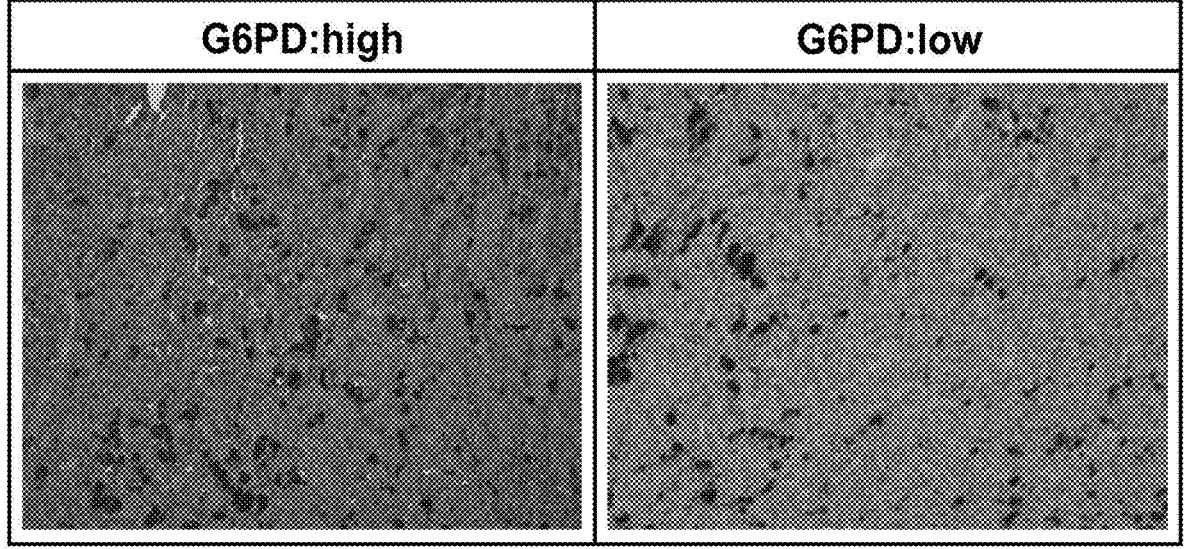
FIG. 9 An explanatory view showing a result of analysis of expression of G6PD by immunohistostaining in malignant melanoma.

FIG. 9 is an explanatory view showing a result of analysis of expression of G6PD by immunohistostaining in malignant melanoma. In FIG. 9, an example of an image of immunohistostaining in a group showing high G6PD expression is shown on the left side of the figure, and an example of an image of immunohistostaining in a group showing low G6PD expression is shown on the right side thereof. The immunohistostaining of G6PD on the samples from the 30 cases presented the results that 12 cases showed high expression of G6PD and that 18 cases showed low expression of G6PD. The expression level of G6PD in immunohistostaining was evaluated by visual observation of stained specimens under a microscope, and a staining rate of 50% or more was defined as high (high expression), and a staining rate of less than 50% was defined as low (low expression).

3. Correlation Between mRNA Expression Level of G6PD and Prognosis

For samples of 17 cases in which no Grade≥3 immune-related adverse event (irAE) was observed upon administration of an immune checkpoint inhibitor, a survival curve was created by the Kaplan-Meier method.

Figure 10:
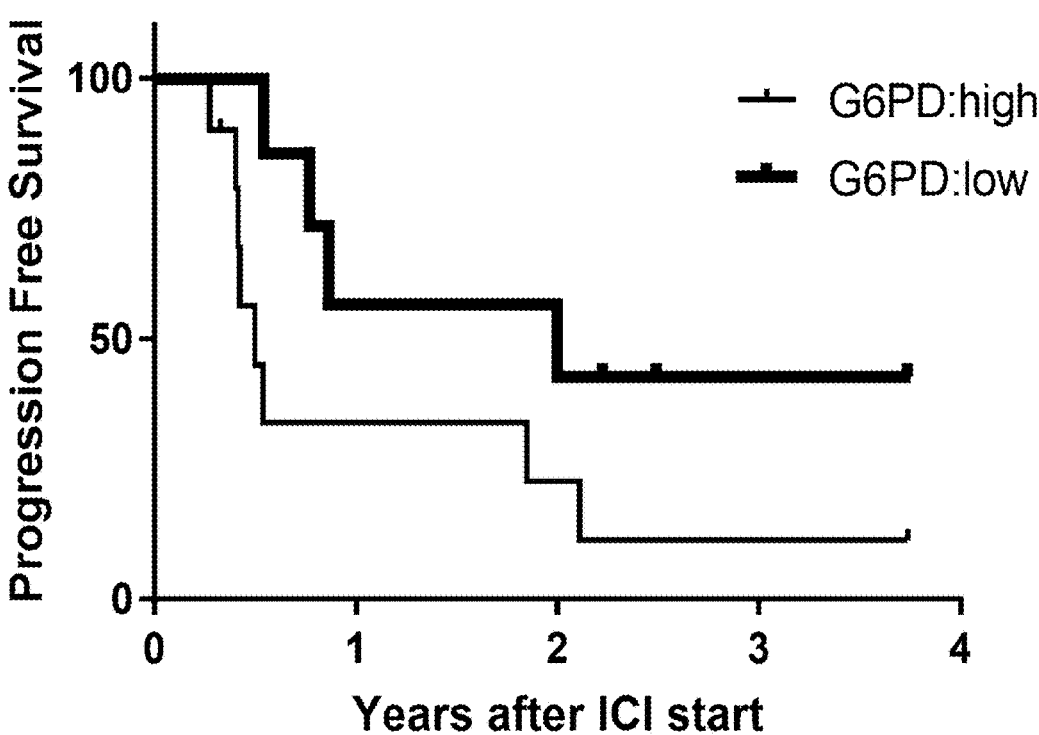
FIG. 10 A view showing a Kaplan-Meier curve of an expression level of G6PD in malignant melanoma.

FIG. 10 is a view showing a Kaplan-Meier curve of the G6PD expression level in malignant melanoma. FIG. 10 shows a Kaplan-Meier curve for the survival rate of each of a group with a high expression level of G6PD and a group with a low expression level of G6PD. In FIG. 10, the group with a high expression level of G6PD is indicated by a thin line, and the group with a low expression level of G6PD is indicated by a thick line. In FIG. 10, the vertical axis represents progression free survival, and the horizontal axis represents the years after ICI start from the start of administration of the immune checkpoint inhibitor. From the results in FIG. 10, it was found that the group with a low G6PD expression level had a higher survival rate, that is, shows a better prognosis than that of the group with a high G6PD expression level. From this, it can be said that the same tendency as in the case where the type of skin cancer was Merkel cell carcinoma was observed also in the case where the type of skin cancer was malignant melanoma. Therefore, it was suggested that, also in malignant melanoma, the expression level of G6PD can be used as an index to predict the prognosis of skin cancer, to evaluate the effectiveness of the immune checkpoint inhibitor, to determine whether the immune checkpoint inhibitor can be administered, to evaluate the malignancy of skin cancer, to predict the possibility of recurrence of skin cancer, and to evaluate the immune activity of skin cancer, as in the case of Merkel cell carcinoma.

4. Relationship Between G6PD Expression Level and Immune-Related Adverse Event

The relationship between the expression level of G6PD and the immune-related adverse event was analyzed. Regarding whether the Grade≥3 immune-related adverse events (irAEs) were observed upon administration of the immune checkpoint inhibitor, analysis was performed on the group with a high expression level of G6PD and the group with a low expression level of G6PD.

Figure 11:
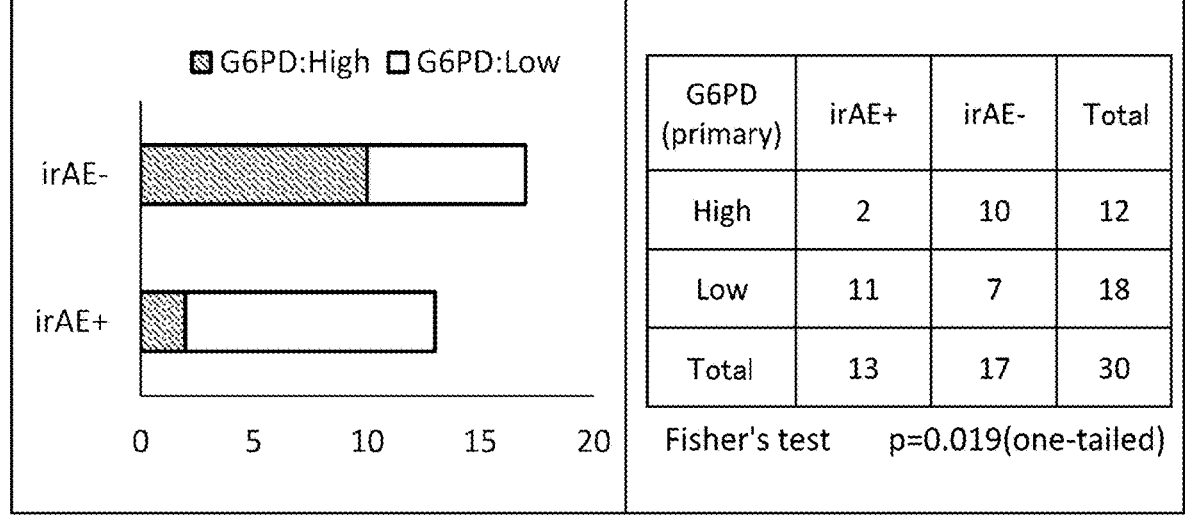
FIG. 11 An explanatory view showing a relationship between presence or absence of Grade≥3 immune-related adverse events and the expression level of G6PD in malignant melanoma.

FIG. 11 is an explanatory view showing a relationship between presence or absence of the Grade≥3 immune-related adverse events and the expression level of G6PD in malignant melanoma. A 2×2 contingency table of the Fisher test regarding the expression level of G6PD and the presence or absence of the Grade≥3 irAEs is shown on the right side of FIG. 11, and a graph created based on the 2×2 contingency table is shown on the left side of FIG. 11. In FIG. 11, the "irAE+" indicates that the Grade≥3 irAEs were observed, and the "irAE−" indicates that no Grade≥3 irAE was observed. From the results shown in FIG. 11, it was found that there were significantly many cases in which the Grade≥3 irAEs were observed in the group with a low expression level of G6PD (p=0.019). That is, when the expression level of G6PD was low, there was observed a significant correlation with a higher possibility of onset of the Grade≥3 irAEs due to the administration of the immune checkpoint inhibitor than that when the expression level of G6PD was high. Therefore, it was found that the expression level of G6PD can be used as an index to predict the possibility of onset of the Grade≥3 irAEs due to the administration of the immune checkpoint inhibitor to patients with skin cancer.

<Cutaneous Angiosarcoma>

1. Sample

As samples, 14 specimens of 7 cases of cutaneous angiosarcoma were used. A method of extracting RNA, a method of next generation sequence analysis, a method of immunohistostaining of G6PD, evaluation criteria for the G6PD expression level, and the like are the same as those described in the Example of Merkel cell carcinoma.

(1) Case A

Case A is a case where the primary lesion was located in the head, and wPTX therapy and radiation therapy were performed as treatment. In Case A, wPTX was administered, but the performance status (PS) deteriorated, and a BSC (best supportive care) policy was adopted. Thereafter, lung metastasis was observed, leading to death of cancer. The OS (overall survival) in Case A was 389 days.

(2) Case B

Case B is a case where the primary lesion was located in the head, and wPTX therapy, radiation therapy, and eribulin therapy were performed as treatment. In Case B, parotid lymph node metastasis was observed during the wPTX administration, and therefore the treatment was changed to eribulin administration, but pneumothorax (PD) was developed. The OS in Case B was 488 days.

(3) Case C

Case C is a case where the primary lesion was located in the head, and surgery, immunotherapy using IL-2, wDTX therapy, wPTX therapy, and radiation therapy were performed as treatment. In Case C, pneumothorax was developed upon administration of wDTX, and therefore the treatment was changed to wPTX administration. This is a case where the administration was discontinued at the patient's request, and the start of chemotherapy was being considered. The OS in Case C was 4826 days or longer.

2. Immunohistostaining

Figure 12:
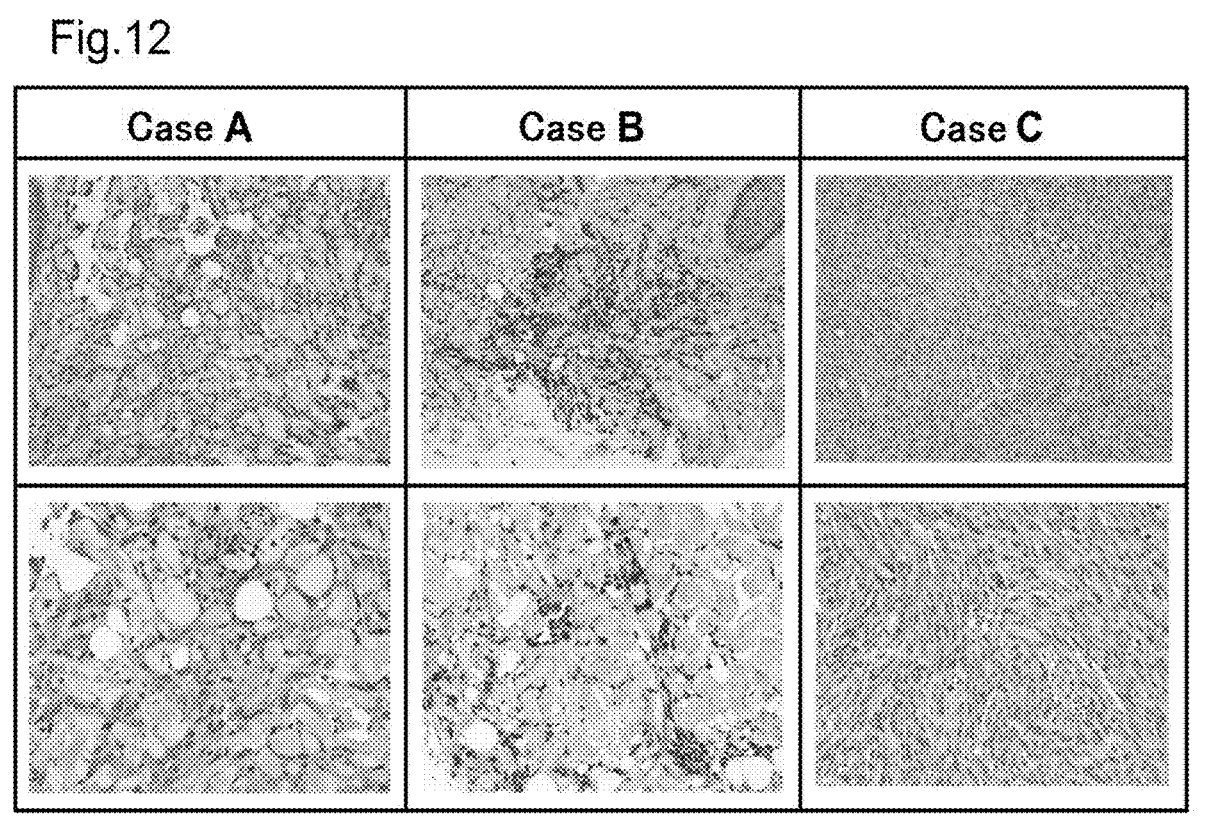

FIG. 12 is an explanatory view showing a result of analysis of expression of G6PD by immunohistostaining in cutaneous angiosarcoma. In FIG. 12, images of immuno-histostaining in Cases A, B, and C of cutaneous angiosar-coma are shown on the upper side of the figure, and enlarged images thereof are shown on the lower side thereof. In Cases A and B, the results obtained by using a biopsy specimen as a sample are shown, and, in Case C, the result obtained by using a surgical specimen as a sample is shown. From the results shown in FIG. 12, it was confirmed that G6PD was highly expressed in Cases A and B, and that G6PD was low expressed in Case C. In addition, from the relationship between the expression level of G6PD and the prognosis, it was suggested that, when the expression level of G6PD is low, a good prognosis is shown, and that, when the expres-sion level of G6PD is high, the prognosis tends to be poor. From this, it can be said that the same tendency as in the case where the type of skin cancer was Merkel cell carcinoma was observed also in the case where the type of skin cancer was cutaneous angiosarcoma. Therefore, it was suggested that, also in cutaneous angiosarcoma, the expression level of G6PD can be used as an index to predict the prognosis of skin cancer, to evaluate the effectiveness of the immune checkpoint inhibitor, to determine whether the immune checkpoint inhibitor can be administered, to evaluate the malignancy of skin cancer, to predict the possibility of recurrence of skin cancer, and to evaluate the immune activity of skin cancer, as in the case of Merkel cell carcinoma.

3. Next Generation Sequence Analysis

Figure 13:
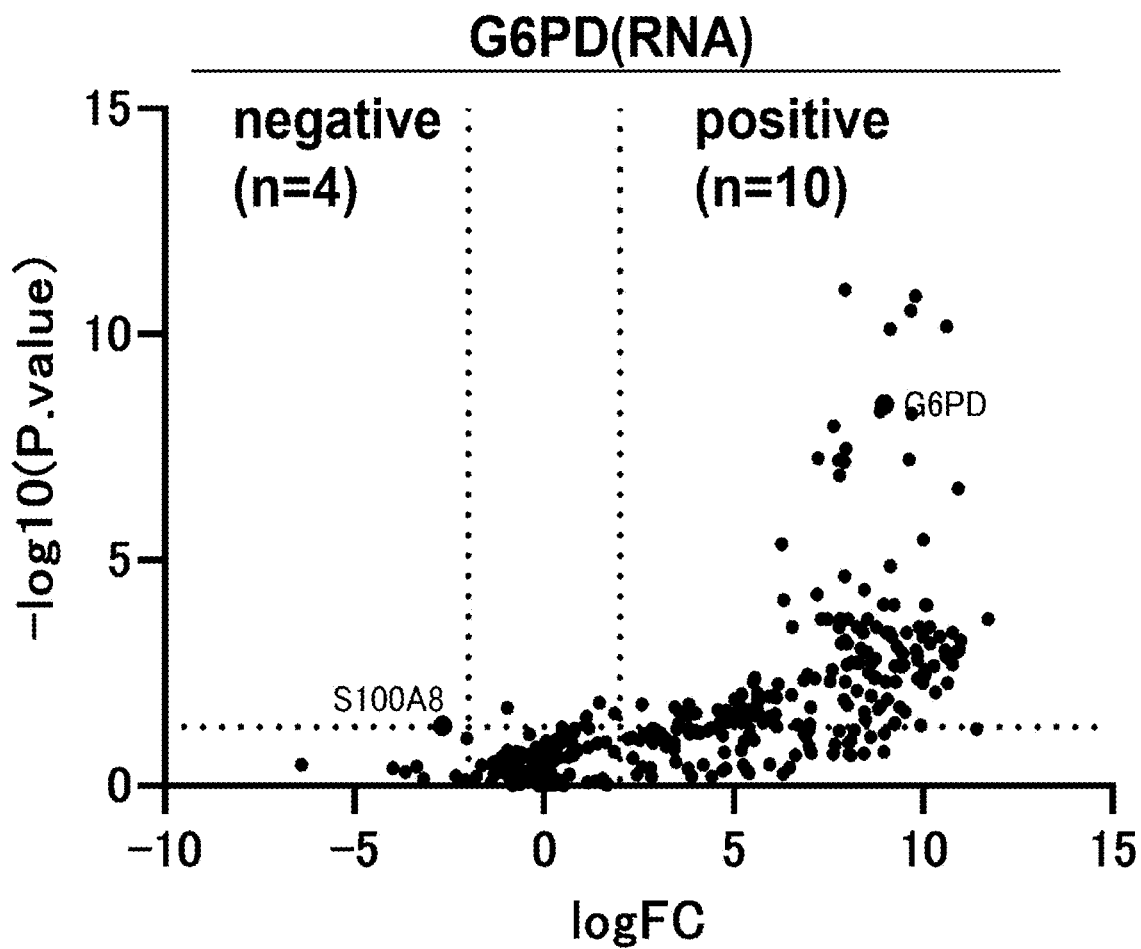
FIG. 13 An explanatory view showing a result of analysis of expression of G6PD by next generation sequence analysis in cutaneous angiosarcoma.

FIG. 13 is an explanatory view showing a result of analysis of expression of G6PD by next generation sequence analysis in cutaneous angiosarcoma. Among the 14 speci-mens used as the samples, 10 specimens were G6PD posi-tive, and 4 specimens were G6PD negative. Here, the G6PD positive indicates that, in the results of immunohistostain-ing, the staining rate of tumor cells is 50% or more, and G6PD is highly expressed. The G6PD negative indicates that, in the results of immunohistostaining, the staining rate of tumor cells is less than 50%, and G6PD is low expressed.

4. GSEA Analysis

For a gene group having a high expression level in the high G6PD expression group, enrichment analysis (gene set enrichment analysis (GSEA analysis)) of the gene list was performed using GSEA software (https://www.gsea-msigd-b.org/gsea/). As the gene set, a c5 Gene Ontology (GO) gene set collection provided by the Molecular Signatures Data-base (MSigDB) was used.

Figure 14:
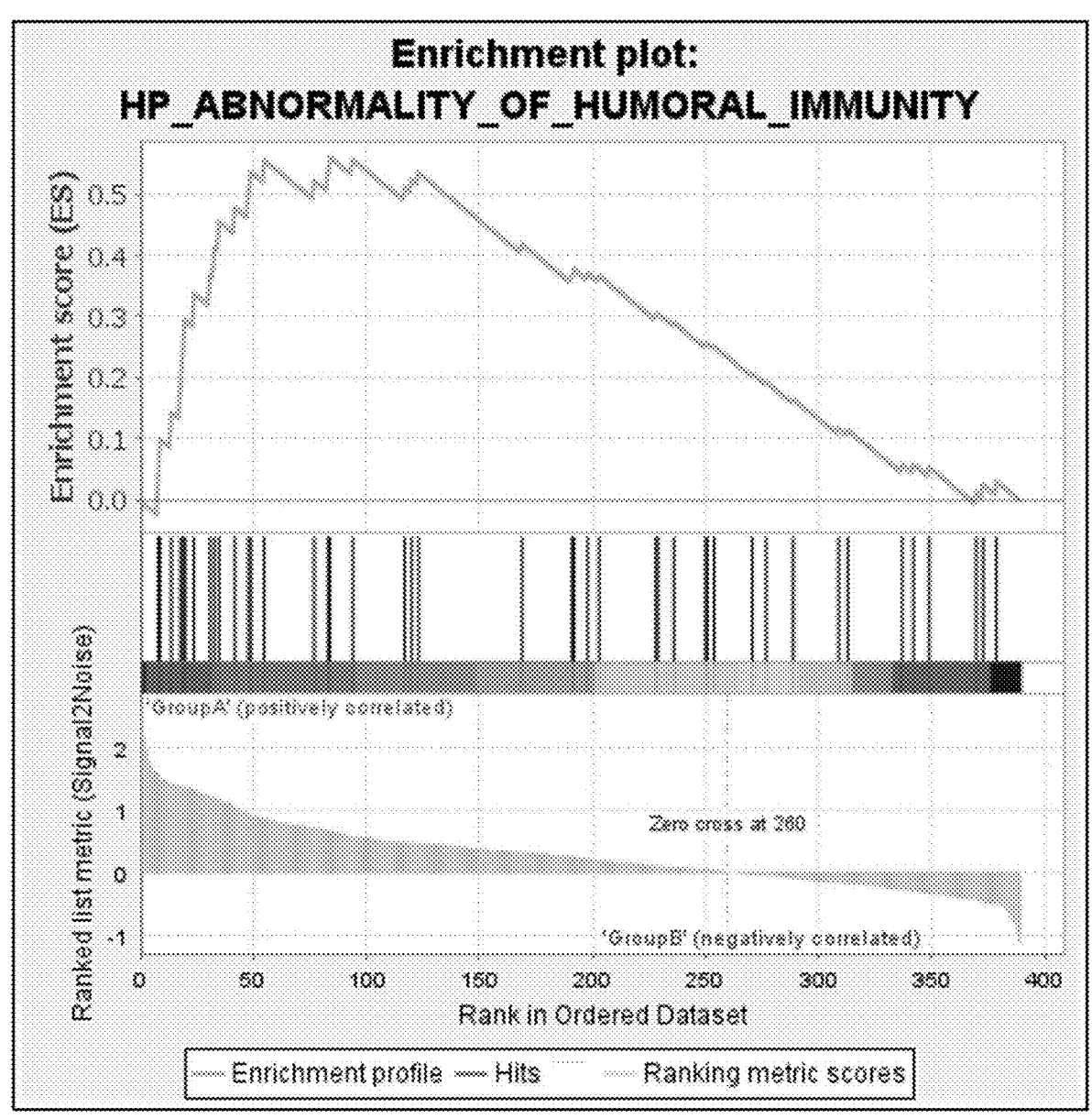
FIG. 14 An explanatory view showing a result of GSEA analysis in a group with a high expression level of G6PD in cutaneous angiosarcoma.
Figure 15:
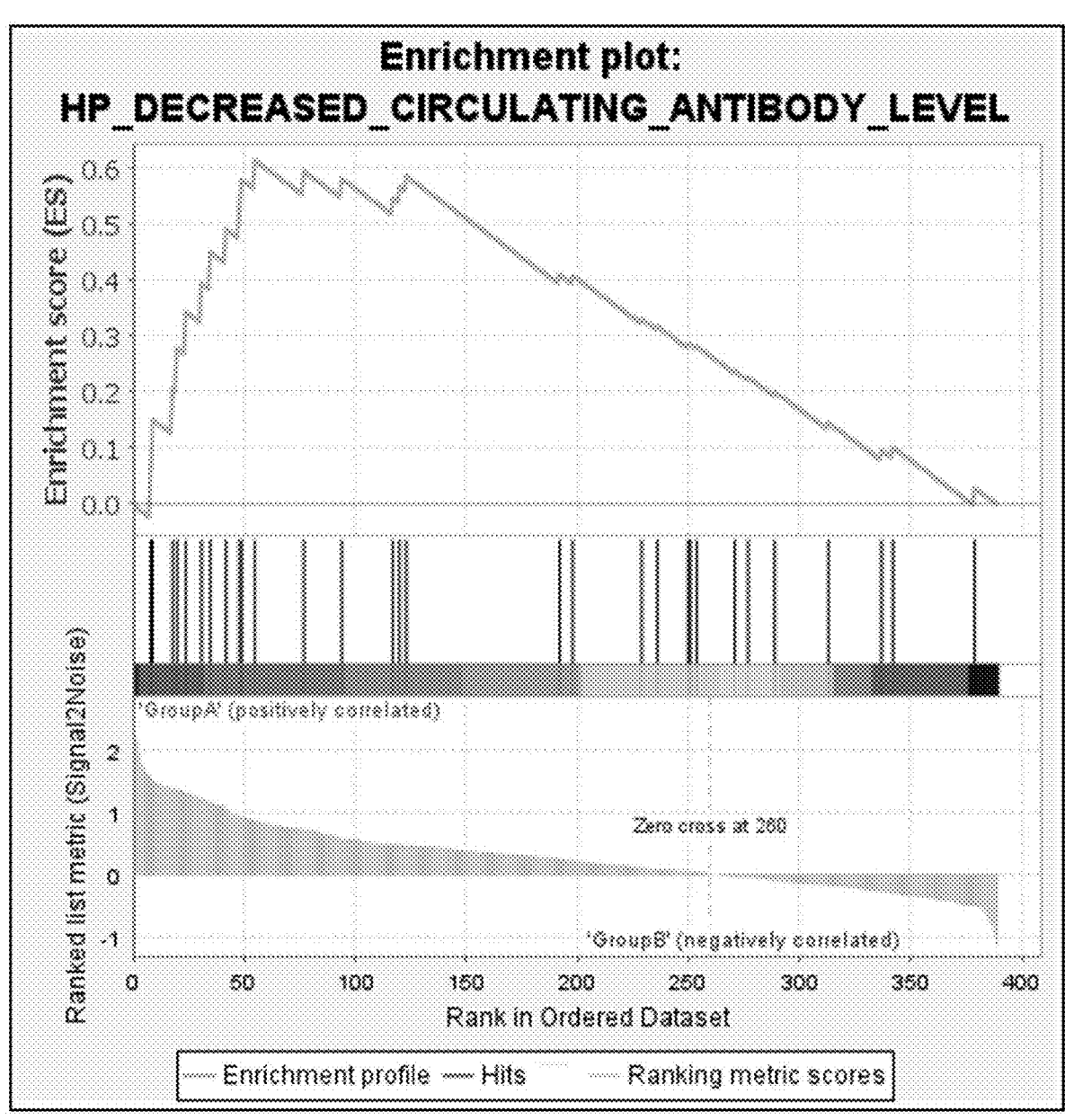
FIG. 15 An explanatory view showing a result of GSEA analysis in the group with a high expression level of G6PD in cutaneous angiosarcoma.

FIGS. 14 and 15 are explanatory views each showing a result of GSEA analysis in the group with a high expression level of G6PD in cutaneous angiosarcoma. From the results shown in FIGS. 14 and 15, it was shown that an abnormality in antibody production was present in the group with a high RNA expression level of G6PD. Therefore, in the group with a high expression level of G6PD, the possibility of reduction in immunity was suggested.

From the results of the Examples described above, it can be said that the same tendency was observed regardless of the type of skin cancer. Therefore, it was suggested that, regardless of the type of skin cancer, the expression level of G6PD can be used as an index to predict the prognosis of skin cancer, to evaluate the effectiveness of the immune checkpoint inhibitor, to determine whether the immune checkpoint inhibitor can be administered, to evaluate the malignancy of skin cancer, to predict the possibility of recurrence of skin cancer, to evaluate the immune activity of skin cancer, and to predict the possibility of onset of Grade≥3 irAEs due to administration of immune checkpoint inhibitors.

The present invention is not limited to the above embodi-ments and examples of the invention at all. Various modi-fications are also included in the present invention as long as they can be easily conceived by those skilled in the art without departing from the scope of the claims.

The invention claimed is:

1. A method of treating skin cancer in a patient, compris-ing determining the expression level of a glucose-6-phos-phate dehydrogenase in a tumor sample collected from said patient by immunohistostaining of the sample, and admin-istering an immune checkpoint inhibitor to said patient if the expression level of said glucose-6-phosphate dehydrogenase is determined by immunohistostaining of the sample to be less than 50% of the staining rate, wherein the immune checkpoint inhibitor is an anti-PD-L1 antibody or an anti-PD-1 antibody.

2. The method of claim 1, wherein said skin cancer is selected from the group consisting of Merkel cell carcinoma, malignant melanoma, squamous cell carcinoma, extramam-mary Paget disease, and cutaneous angiosarcoma.

3. The method of claim 2, wherein said skin cancer is Merkel cell carcinoma.

4. The method of claim 1, wherein the immunohistostain-ing of the sample is by visual observation of stained speci-mens under a microscope.

5. The method of claim 1, wherein said immune check-point inhibitor is Avelumab.

6. A method of treating skin cancer in a patient, compris-ing determining the expression level of a glucose-6-phos-phate dehydrogenase in a sample collected from said patient by immunohistostaining of the sample based on an antigen-antibody reaction using an anti-G6PD antibody or a frag-ment thereof, and administering an immune checkpoint inhibitor to said patient if the expression level of said glucose-6-phosphate dehydrogenase is determined by immunohistostaining of the sample to be less than 50% of the staining rate, wherein the skin cancer is selected from the group consisting of Merkel cell carcinoma, malignant mela-noma, and cutaneous angiosarcoma, wherein the immune checkpoint inhibitor is an anti-PD-L1 antibody or an anti-PD-1 antibody.

7. The method of claim 6, wherein said immune check-point inhibitor is an anti-PD-L1 antibody.

8. The method of claim 6, wherein said immune check-point inhibitor is Avelumab.

9. The method of claim 6, wherein said skin cancer is Merkel cell carcinoma.

10. The method of claim 6, wherein said skin cancer is malignant melanoma.

11. The method of claim 6, wherein said skin cancer is cutaneous angiosarcoma.

* * * * *